United States Patent
Nonomura (12)

(10) Patent No.: US 6,258,749 B1
(45) Date of Patent: Jul. 10, 2001

(54) METHODS FOR TREATING PLANTS AND ENHANCING PLANT GROWTH USING POLYACYLGLYCOSIDES AND/OR POLYALKYLGLYCOSIDES AND FORMULATIONS FOR SAME

(75) Inventor: Arthur M. Nonomura, Boxborough, MA (US)

(73) Assignee: The Dow Chemical Company, Midland, MI (US)

( * ) Notice: Subject to any disclaimer, the term of this patent is extended or adjusted under 35 U.S.C. 154(b) by 0 days.

(21) Appl. No.: 09/510,696

(22) Filed: Feb. 22, 2000

(51) Int. Cl.$^7$ ..................................... A01N 43/16
(52) U.S. Cl. .................. 504/121; 504/124; 504/125; 504/292
(58) Field of Search ................... 504/292, 121, 504/124, 125

(56) References Cited

U.S. PATENT DOCUMENTS

| | | | |
|---|---|---|---|
| H224 | 3/1987 | Malik et al. | 71/92 |
| H303 | 7/1987 | Malik et al. | 514/85 |
| 4,764,201 | 8/1988 | Iino et al. | 71/77 |
| 5,177,307 | 1/1993 | Houck et al. | 800/205 |
| 5,549,729 | 8/1996 | Yamashita | 71/26 |
| 5,578,552 | 11/1996 | Katayama et al. | 504/285 |
| 5,919,998 | 7/1999 | Bandurski et al. | 800/286 |
| 5,958,104 | 9/1999 | Nonomura et al. | 71/11 |

OTHER PUBLICATIONS

Physiologia Plantarium 75: 511–517. Copenhagen 1989; "Cytokinin cocentration in relation to mineral nutrition and benzyladenine treatment in *Plantago Major* ssp. *pleiosperma*": Kuiper et al.

Proc. Natl.AcadSci.Vol. 96,pp. 284–289, Jan. 1999 Plant Biology; "Isolation of a cytokinin gene, ZOG1, encoding zeatin O–glucosyltransferase from *Phaseoulus lunatus*"; Martin et al.

The Plant Journal (1996), 36–46; "Chemically induced expression of the rolC–encoded β–glucosidase in transgenic tobacco plants and analysis of cytokinin metabolism: rolC does not hydrolyze endogenous cytokinin glucosides in planta"; Faiss, et al.

J.Agric.Food Chem., vol. 45, No. 7, 1997 pp. 2763–2767; "Effects of Foliar Applications of Carbohydrates on the Yield of Cotton (*Gossypium hirsutum*) Lint": Hedin et al.

Robert: Syntheses of Glucosides. Part 1. 1937.

J. Jasik et al. Plant Science 124 (1997) 57–68; "Characertisation of morphology and root formation in the model woody perennial shrub . . . ".

*Primary Examiner*—S. Mark Clardy

(57) ABSTRACT

Methods and formulations for treating plants and enhancing plant growth and for safening high concentrations of one or more phytocatalysts, wherein one or more formulations, comprising, a high concentration of one or more phytocatalysts, and an effective amount of one or more polyacylglycosides and polyalkylglycosides; and isomers, and metabolites, salts, hydrates, esters, amines, and derivatives of the polyacylglycosides and polyalkylglycosides, and combinations thereof, is applied to the plants.

63 Claims, No Drawings

METHODS FOR TREATING PLANTS AND ENHANCING PLANT GROWTH USING POLYACYLGLYCOSIDES AND/OR POLYALKYLGLYCOSIDES AND FORMULATIONS FOR SAME

FIELD OF THE INVENTION

This invention relates to methods and formulations for treating plants and enhancing plant growth and for safening high concentrations of phytocatalysts, such as ammonium, using polyacylglycosides and/or polyalkylglycosides and more specifically to methods for treating plants and enhancing plant growth with formulations comprising high concentrations of ammonium and one or more polyacylglycosides and/or polyalkylglycosides.

BACKGROUND OF THE INVENTION

The growth of plants is dependent on the synthesis of polysaccharides, especially, cellulose in cell walls. Innumerable methods and compositions have been proposed and/or developed to enhance the synthesis of these polysaccharides and thereby promote plant growth. Over the years, much of this development has focused on applying plant growth regulators (PGRs), such as auxins, cytokinins, gibberellins and brassinolides, to plants. Vitamin K and derivatives thereof have also been considered for use as a plant growth regulator as taught by Iino et al. in U.S. Pat. No. 4,764,201. However, field results using PGRs has, at best, been mixed. Further, PGRs, such as the derivatives of vitamin K proposed by Iino et al., are cost-prohibitive for practical applications. More recently, researchers are also considering genetic manipulation and related techniques to alter or otherwise enhance the growth patterns of plants. At present, many of these techniques are not yet applicable to field production and are typically limited to a specific type of plant.

Whether using a plant growth regulator or a genetically altered plant, any number of agronomically suitable additives, adjuvants and/or phytocatalysts are applied to the plants to support or enhance plant growth, including: fertilizers containing elements such as nitrogen, phosphorus, potassium, elevated carbon dioxide, hydrogen peroxide, iron and manganese; secondary nutrients such as sources of sulfur, calcium, and magnesium; micronutrients, such as boron, cobalt, copper, molybdenum, zinc, nickel; water soluble carbohydrates such as sucrose, fructose and glucose as described in U.S. Pat. No. 5,549,729; and various alkyl glucosides as described in U.S. Pat. No. 5,958,104.

Several of the phytocatalysts are particularly important, such as iron, manganese and an ammoniacal nitrogen source such as ammonium. However, it is known that high doses of these phytocatalyst nutrients are lethal to plants because the plants are not able to metabolize the nutrients at a sufficient rate. For example, it is known that, under conventional conditions of plant culture, ammonium is phytotoxic to plants at high concentrations as described by Robert M. Devlin et al., *Photosynthesis*, pp. 270–277 (Van Nostrand Reinhold Co. 1971). Devlin et al. found that a high concentration of ammonium elicits a plant response akin to various nutrient deficiencies. Further, ammonium ions are known to inhibit photophosphorylation and subsequent carbon dioxide fixation and, at very high concentrations, to impair photosynthesis in intact leaves.

Since high concentrations of ammonium reduce plant growth, the amount of ammonium used is typically limited to less than one third of the total source of nitrogen. See, Roy A. Larson, *Introduction to Floriculture*, 2d. Edition, p. 464 (Academic Press 1992). The recommended optimal nitrate-N concentrations are between 100 to 199 ppm for most horticultural applications. See, Id. and Vic Ball, *Ball RedBook*, 15th Edition, p. 246 (Geo J. Ball 1991). The generally accepted upper limit for nitrogen fertilizer is between about 300 ppm to 400 ppm. Concentrations above this range are considered toxic to plants. Thus, applying ammonium to treat plants and facilitate plant growth has until now been limited to low concentrations. Methods and formulations for safening high concentrations of manganese with alkyl glycosides are disclosed by A. Nonomura in U.S. patent application Ser. No. 09/448,345, filed on Nov. 23, 1999 and are incorporated herein by reference.

SUMMARY OF THE INVENTION

It is a primary object of the invention to provide methods and formulations for treating plants and enhancing plant growth and for safening high concentrations of phytocatalysts, such as ammonium, by applying a formulation, comprising one or more polyacylglycosides and/or polyalkylglycosides, to the plants.

It is a further object of the invention to provide methods and formulations for treating plants and enhancing plant growth and for safening high concentrations of phytocatalysts, such as ammonium, by applying a formulation, comprising one or more polyacylglycosides, to the plants.

It is a further object of the invention to provide methods and formulations for treating plants and enhancing plant growth and for safening high concentrations of phytocatalysts, such as ammonium, by applying a formulation, comprising an effective amount of glucose pentaacetate, to the plants.

It is a further object of the invention to provide methods and formulations for safening high concentrations of ammonium, in a range between about 500 ppm to 2500 ppm of ammonium ions, for treating plants and enhancing plant growth.

It is a further object of the invention to provide methods and formulations for safening high concentrations of phytocatalysts, including, but not limited to, ammonium and manganese, for treating plants and enhancing plant growth.

It is a further object of the invention to provide methods and formulations for treating plants and enhancing plant growth by applying a formulation, of high concentrations of ammonium with one or more polyacylglycosides and/or polyalkylglycosides, to the plants.

It is a further object of the invention to provide methods and formulations for treating plants and enhancing plant growth using one or more polyacylglycosides and/or polyalkylglycosides, which are more potent than monoalkyl- and monoacylglycosides and more cost effective than cyclicalkylglycosides and cyclicacylglycosides and vitamin K and derivatives thereof.

In crops, such as rice, yields have proven to be carbon sink limited. Cellulose is the largest sink in any plant and the application of polyalkylglycosides and/or polyacylglycosides to allocate carbon into the largest sink may open crops to the proportionate enhancement of yield potential. See e.g., J. C. Waterlow et al., "Applications of science to increase yield", Chapter III, *Feeding a World Population of More Than Eight Billion People* (Oxford Univ. Press, 1998).

The methods and formulations of the invention are used to activate plant growth in a manner similar to the Rhizobial synergistic mode of activity, where the plant provides the Rhizobia with sugar and, in turn, the Rhizobia provide the plant host with ammonia. Thus plant growth is artificially signaled and activated by simulating a plant's nodulation (Nod) response to Rhizobia. For illustration, chitooligosaccharide (CO) compounds, tetra-N-acetylchitotetraose and octa-N-acetylchitooctaose, are known to elicit plant defense systems. Ryan, C. A., *Biochemisty*, 27:8879 (1988). Tetra-N-acetylchitotetraose is a component of the lipo-chitooligosaccharides (LCOs) secreted from Rhizobia. Synthetic LCO compounds act as signaling molecules in the host plant. Rohrig, H., et al., *Science*, 269:841 (1995). Tetra-N-acetylchitotetraose is also a substrate for the Rhizobium leguminosarum nodulation protein NodB, a CO deacetylase. John, M., et al., *Proceedings of the National Academy of Sciences*, 90:625 (1993). Similarly, penta-N-acetylchitotetraose is a substrate for the Rhizobium leguminosarum nodulation protein NodL. Bloemberg, G. V., et al., *Molecular Microbiology*, 11:794 (1994). Recombinant NodB deacetylates the acetylglucosamine residue of the CO, but does not deacetylate the monoacylmonosaccharide, N-acetylglucosamine.

The formulations of the invention effectively mimic the poly-N-acetylchitotetraose structure without the high molecular weight, which would otherwise interfere with cell membrane penetration, and without the high degree of specificity associated with Nod proteins. Further, the polyacylglycosides and polyalkylglycosides are sufficiently similar to effectively mimic LCO-signal transduction, leading to cell division and enhanced plant growth.

The methods and formulations of the invention exogenously provide simple artificial sugar substrates that trigger natural defensive responses to natural larger molecules; and further more, by exogenously providing ammonia, which normally is supplied to the plant by Rhizobial symbionts, the overall growth of the plant is enhanced. In contrast to the larger, naturally occurring molecules, such as the LCOs, typically associated with the activation of Nod signals, the compounds used in the methods and formulations of the invention represent the smallest and most active portion of these larger signal molecules. As such, the methods and formulations of the invention provide inexpensive, artificial mimics of the naturally occurring, larger, expensive and therefore, commercially impractical, Nod signaling LCOs.

For example, one of the smallest and preferred portions of the LCO agents are the simple $(acyl)_n$-glycosides, where n=2 to 5, and preferably where n=5. The glucose pentaacetates are the most preferred of these compounds and are inexpensive to manufacture using glucose and acetic anhydride as the raw materials. Glucose pentaacetate may be used in practical dosages ranging, for example, from 260 ppm for corn to 1200 ppm for Canola.

A preferred method of the invention for treating plants and enhancing plant growth, comprises the step of, applying an effective amount of one or more polyacylglycosides to the plants.

Another preferred method of the invention for treating plants and enhancing plant growth, comprises the step of, applying an effective amount of glucose pentaacetate to the plants, wherein the glucose pentaacetate preferably comprises $\beta$-D-glucose-$(acetate)_5$ and/or $\alpha$-D-glucose-$(acetate)_5$.

A preferred method of the invention for safening high concentrations of one or more phytocatalysts for treating plants and enhancing plant growth, comprises the steps of: applying one or more phytocatalysts comprising ammonium ions at a concentration between about 500 parts per million (ppm) and 2500 ppm to the plants; and applying an effective amount of one or more compounds selected from a group consisting of polyacylglycosides and polyalkylglycosides; isomers, metabolites, salts, hydrates, esters, amines, and derivatives of the polyacylglycosides, and polyalkylglycosides; and combinations thereof; to the plants; wherein the effective amount of the compounds is preferably between about 100 ppm to 10,000 ppm concentration. One or more of the compounds preferably comprises pentaacetylglycoside, wherein the effective amount of the pentaacetylglycoside is preferably between about 3 ppm to 3000 ppm, and more preferably between about 100 ppm and 1500 ppm.

The phytocatalysts of the invention may further comprise one or more nutrients selected from a group consisting of iron and manganese, wherein the manganese is preferably applied at a concentration between about 2 to 100 ppm. The method may also further comprise the steps of applying one or more plant growth regulators to the plant, and/or applying the compounds to the plants as a foliar formulation with one or more surfactants, wherein one or more of the surfactants preferably comprises an ammonium salt, and more specifically, wherein one or more of the surfactants preferably comprises an ammonium salt of a fatty acyl sarcosinate. The ammonium salt of the surfactant may be applied in an amount between about 1 to 2 grams/liter.

Another preferred method of the invention for safening high concentrations of one or more phytocatalysts for treating plants and for enhancing plant growth, comprises the steps of: applying one or more phytocatalysts comprising ammonium ions at a concentration between about 500 parts per million (ppm) and 2500 ppm to the plants; and applying an effective amount of one or more $(acyl)_n$glycosides, wherein n=2 to 5; isomers, metabolites, salts, hydrates, esters, amines, and derivatives of the $(acyl)_n$glycosides; and combinations thereof, to the plants, wherein the $(acyl)_n$ glycosides may comprise $\beta$-D-glucose-$(acetate)_5$ and/or $\alpha$-D-glucose-$(acetate)_5$.

Yet another preferred method of the invention for safening high concentrations of one or more phytocatalysts for treating plants and for enhancing plant growth, comprises the steps of: applying one or more phytocatalysts comprising ammonium ions at a concentration between about 500 parts per million (ppm) and 2500 ppm to the plants; and applying an effective amount of one or more $(acyl)_n$glycosamines, wherein n=2 to 5; isomers, metabolites, salts, hydrates, esters, amines, and derivatives of the $(acyl)_n$glycosamines; and combinations thereof, to the plants, wherein one or more of the $(acyl)_n$glycosamines preferably comprises $\beta$-D-glucosamine pentaacetate, and wherein one or more of the phytocatalysts also comprises iron and manganese, wherein the manganese is applied at a concentration between about 2 to 100 ppm. The method may further comprise the step of applying one or more surfactants, wherein one or more of the surfactants may comprise an ammonium salt.

Yet another preferred method of the invention, for safening high concentrations of one or more phytocatalysts for treating plants and for enhancing plant growth, comprises the steps of: applying one or more phytocatalysts comprising ammonium ions at a concentration between about 500 parts per million (ppm) and 2500 ppm to the plants; and applying an effective amount of one or more $(methyl)_n$ glycosides, wherein n=2 to 5; and isomers, metabolites, salts, hydrates, esters, amines and derivatives of the $(methyl)_n$ glycosides; to the plants, wherein one or more of the $(methyl)_n$ glycosides preferably comprises $(methyl)_4$-D-glucopyranose, and, wherein one or more of the phytocatalysts may further comprise iron and manganese.

A preferred formulation of the invention for treating plants and for enhancing plant growth, comprises, an effective amount of one or more compounds selected from a group consisting of, (acyl)$_n$ glycosides, wherein n=2 to 5; isomers, metabolites, salts, hydrates, esters, amines, and derivatives of said (acyl)$_n$glycosides; and combinations thereof, wherein one or more of the compounds preferably comprises β-D-glucose-(acetate)$_5$ and/or α-D-glucose-(acetate)$_5$.

A preferred formulation of the invention for safening high concentrations of one or more phytocatalysts for treating plants and enhancing plant growth, comprises: one or more phytocatalysts comprising ammonium ions at a concentration between about 500 parts per million (ppm) and 2500 ppm; and an effective amount of one or more compounds selected from a group consisting of polyacylglycosides and polyalkylglycosides; isomers, metabolites, salts, hydrates, esters, amines, and derivatives of the polyacylglycosides and polyalkylglycosides; and combinations thereof, wherein the effective amount of the compounds preferably comprises between about 100 ppm to 10,000 ppm concentration. One or more of the compounds preferably comprises polyacylglycoside, and more specifically, preferably comprises pentaacetylglycoside, wherein the effective amount of the pentaacetylglycoside is preferably between about 3 ppm to 3000 ppm and more preferably between about 100 ppm and 1500 ppm.

The formulation may also comprise one or more phytocatalysts comprising one or more nutrients selected from a group consisting of iron and manganese, wherein the manganese is applied at a concentration between about 2 to 100 ppm; one or more plant growth regulators; and/or one or more surfactants, wherein one or more of the surfactants preferably comprises an ammonium salt, such as a fatty acid sarcosinate. The preferred amount of the ammonium salt of the surfactant is between about 1 to 2 grams/liter.

Another preferred formulation of the invention for safening high concentrations of one or more phytocatalysts for treating plants and for enhancing plant growth, comprises: one or more phytocatalysts comprising ammonium ions at a concentration between about 500 parts per million (ppm) and 2500 ppm; and an effective amount of one or more compounds selected from a group consisting of, (acyl)$_n$glycosides, wherein n=2 to 5; isomers, metabolites, salts, hydrates, esters, amines, and derivatives of the (acyl)$_n$glycosides; and combinations thereof, wherein one or more of the compounds preferably comprises β-D-glucose-(acetate)$_5$ and/or α-D-glucose-(acetate)$_5$.

Yet another formulation of the invention for safening high concentrations of one or more phytocatalysts for treating plants and for enhancing plant growth, comprises: one or more phytocatalysts comprising ammonium ions at a concentration between about 500 parts per million (ppm) and 2500 ppm; and an effective amount of one or more compounds selected from a group consisting of, (acyl)$_n$glycosamines, wherein n=2 to 5; isomers, metabolites, salts, hydrates, esters, amines, and derivatives of the (acyl)$_n$glycosamines; and combinations thereof, wherein one or more of the compounds preferably comprises β-D-glucosamine pentaacetate.

The phytocatalyst may likewise further comprise iron and manganese, wherein the manganese is preferably at a concentration between about 2 to 100 ppm. The formulation may also likewise comprises one or more surfactants, wherein one or more of the surfactants preferably comprises an ammonium salt.

Yet another preferred formulation of the invention for safening high concentrations of one or more phytocatalysts for treating plants and for enhancing plant growth, comprises: one or more phytocatalysts comprising ammonium ions at a concentration between about 500 parts per million (ppm) and 2500 ppm; and an effective amount of one or more compounds selected from a group consisting of, (methyl)$_n$glycosides, wherein n=2 to 5; and isomers, metabolites, salts, hydrates, esters, amines and derivatives of the (methyl)$_n$ glycosides, wherein one or more of the compounds preferably comprises (methyl)$_4$-D-glucopyranose.

DETAILED DESCRIPTION OF THE PREFERRED METHODS AND FORMULATIONS

As noted, the methods and formulations of the invention are designed to treat plants and to enhance plant growth. Treatment and plant growth enhancement are generally achieved by formulating one or more polyalkylglycosides and/or polyacylglycosides with one or more phytocatalysts and with or without one or more PGRs and applying the formulation in a dry or liquid form directly to the plants and/or the plant culture media.

Unless otherwise defined, all technical and scientific terms employed herein have their conventional meaning in the art. As used herein, the following terms have the meanings ascribed to them.

"Enhance(s) growth" or "enhancing growth" refers to promoting, increasing or improving the rate of growth of the plant or increasing or promoting an increase in the size of the plant.

"Plant" refers to any life form which synthesizes cellulose including, but not necessarily limited to: microbials including prokaryotes, eukaryotes, bacteria, algae, lichens and fungi; cryptophytes; angiosperms; and gymnosperms. The methods and formulations of the inventions are advantageous for many applications including, but not limited to, agricultural, horticultural, maricultural, floricultural and silvicultural applications.

"Surfactant" refers to surface-active agents, i.e., which modify the nature of surfaces, often by reducing the surface tension of water. They act as wetting agents, spreaders, dispersants, or penetrants. Typical classes include cationic, anionic (e.g., alkylsulfates), nonionic (e.g., polyethylene oxides) and ampholytic. Soaps, alcohols, block copolymers and polysiloxanes are other examples.

"Aqueous", with reference to solutions or solvents, refers to solutions or solvent systems which consist primarily of water, normally greater than 50 weight percent water, and can be essentially pure water in certain circumstances. For example, an aqueous solution or solvent can be distilled water, tap water, irrigation water, well water or the like. However, an aqueous solution or solvent can include water having substances such as pH buffers, pH adjusters, organic and inorganic salts, alcohols (e.g., ethanol), sugars, amino acids, or surfactants incorporated therein. The aqueous solution or solvent may also be a mixture of water and minor amounts of one or more cosolvents, including agronomically suitable organic cosolvents, which are miscible therewith, or may form an emulsion therewith. Agronomically suitable organic solvents include, for example, acetone, methanol, limonene, paraffin oils, silanes, esters, ethers, and emulsifiers.

"Percent" or "%" is percent by weight unless otherwise indicated.

"Ppm" refers to parts per million by weight.

"M" refers to molar concentration and "mM" refers to millimolar concentration.

"PGR" refers to a plant growth regulator.

"PGRs" is the plural of PGR.

"Auxin" is a plant hormone that is currently classified as a PGR which is physiologically active at 0.1 to 1 ppm concentrations as a cell elongation factor or rooting stimulant found in plants.

"Cytokinin" refers to a PGR, generally with an adenine nucleus, that is physiologically active at very low concentration as a cell division factor found in plants and yeast.

"CPGR" refers to a conjugated plant growth regulator.

"TAG" refers to tetraacetylglucoside.

"Alkylglycoside" refers to glycoside conjugated alkyls that are saturated or unsaturated; and may be cyclic, heterocyclic, aromatic, substituted aromatic, or heteroaromatic; and any combination thereof.

"Polyalkylglycoside" refers to glycoside conjugated compounds comprising two or more alkyl groups and combinations thereof.

"Acylglycoside" refers to glycoside conjugated acyls that are saturated or unsaturated; and may be cyclic, heterocyclic, aromatic, substituted aromatic, or heteroaromatic; and any combination thereof.

"Polyacylglycoside" refers to glycoside conjugated compounds comprising two or more acyl groups and combinations thereof.

"Acylglycosamine" refers to glycosamine conjugated acyls that are saturated or unsaturated; and may be cyclic, heterocyclic, aromatic, substituted aromatic, or heteroaromatic; and any combination thereof.

"Polyacylglycosamine" refers to glycosamine conjugated compounds comprising two or more acyl groups and combinations thereof.

The formulations of the invention may be applied to all parts of the plant including the leaves, shoots, roots, stems, flowers and fruits, depending on the nature of the formulation utilized, using conventional application techniques. Plants nearing or at maturity may be treated at any time before and during seed development. Fruit bearing plants may be treated before or after the onset of bud or fruit formation. Improved growth occurs as a result of the exogenous application of high concentrations of ammonium with one or more polyacylglycoside and/or polyalkylglycosides, and other appropriate nutrients and additives such as soluble iron and high concentrations of manganese.

Polyacylglycosides and Polyalkylglycosides

Polyacylglycosides and polyalkylglycosides useful in the formulations and methods of the invention include, but are not necessarily limited to any, (Alkyl)$_n$ glycoside, wherein n=2 to 5, its salts and its derivatives, and (Acetyl)$_n$ glycoside, wherein n=2 to 5, its salts and its derivatives, including, but not limited to, Methyltriacetyl glucoside Pentaacetyl glycopyranose Pentaacetylglucopyranose Pentaacetylgalactopyranose Pentaacetylmannopyranose Phenyltetraacetylglucoside Sucrose octaacetate Tetraacetylglycoside Tetraacetylglucoside Tetraacetylglucopyranose Tetraacetylmannopyranose Tetraacetylribofuranose Tetraacetylfucopyranose Tetraacetylxylopyranose Tetradecylmaltoside Tetramethylglycoside Triacetylglycopyranose Triacetylfucopyranosyl chloride Triacetyladenosine Any other polyacyl or polyalkyl conjugated to one or more pyranose, furanose, and/or cyclic or straight chain sugar, including, but not necessarily limited to the following sugars:

Aldoses, such as, glyceraldehyde erythrose threose ribose arabinose xylose lyxose allose altrose glucose mannose gulose idose galactose talose Ketoses, such as, dihydroxyacetone erythrulose ribulose xylulose psicose fructose sorbose tagatose Glucopyranose Fructofuranose Fructopyranose Xylopyranose and their derivatives, e.g., glucuronides, glucosamines, Any polyacylpolysaccharide or polyalkylpolysaccharide, and Any isomer, metabolite, salt, hydrate, ester, amine, surfactant-linked derivative and other suitable biologically or chemically equivalent derivative, and combination thereof.

Polyacyl Amine Derivatives

Polyacyl amine derivatives useful in the formulations and methods of the invention include, but are not necessarily limited to, (Acetyl)$_n$ glycosamine, wherein n=2 to 5, its salts and its derivatives, including, but not limited to, Methyltriacetyl glucosamine Pentaacetylglycosamine Pentaacetylglucosamine Pentaacetylgalactosamine Pentaacetylmannosamine Phenyltetraacetylglucosamine Tetraacetylglycosamine Tetraacetylglucosamine Tetraacetylglucosamine Tetraacetylmannosamine
Tetraacetylribosamine
Tetraacetylfucosamine
Tetraacetylxylosamine Tetradecylmaltosamine Tetramethylglycosamine Triacetylglycosamine
Triacetylfucosamine chloride Triacetyladenosine Any other polyacyl amine derivative conjugated to one or more pyranose, furanose, and/or cyclic or straight chain sugar, including, but not necessarily limited to the following sugars:

Aldoses, such as,
glyceraldehyde
erythrose
threose
ribose
arabinose
xylose
lyxose
allose
altrose
glucose
mannose
gulose
idose
galactose
talose Ketoses, such as,
dihydroxyacetone
erythrulose
ribulose
xylulose
psicose
fructose
sorbose
tagatose Glucopyranose Fructofuranose Fructopyranose Xylopyranose and their derivatives, e.g., glucuronides, glucosamines, Any polyacylglycosamine isomer, metabolite, salt, hydrate, ester, amine, surfactant-linked derivative and other suitable biologically or chemically equivalent derivative and combination thereof.

Phytocatalysts

The phytocatalysts of the formulations and methods of the invention comprise ammoniacal nitrogen and preferably further comprise, manganese and iron in forms which are available to plants, which include, but are not necessarily limited to:

Ammoniacal Nitrogen
Ammonium salts including, but not limited to:
Ammonium sulfate
Ammonium nitrate
Ammonium formate
Ammonium hydroxide
Ammonium chloride
Urea
Formaldehyde urea
Amino Acid
Protein
Peptide
Manure
Guano
Manganese
Manganese salt
Manganese chelate
Mn-EDTA
Mn-HEDTA
Mn-EDDHA
Iron
Ferric salt
Ferrous salt
Ferrous chelate
Ferric chelate
Fe-EDTA
Fe-HEDTA
Fe-EDDHA; and and any others, such as those listed in the Western Fertilizer Handbook.

The formulations and methods of the present invention may be applied to virtually any variety of living organism which synthesizes cellulose. Such organisms include innumerable agricultural plants, such as those listed by G. M. Markle, J. J. Baron and B. A. Schneider, *Food and Feed Crops of the United States,* (Meister Publishing 1998); and by Mark Griffiths, *Index of Garden Plants,* (Timber Press 1994). Further, plants which may benefit according to the present invention include, but are not limited to, all plants that have been genetically modified, including hybridized, chimeric, transgenic, cross-bred and mutated plants, and plants comprising recombinant DNA or RNA or plants that have otherwise had their DNA or RNA modified. These lists are intended to be exemplary and are not intended to be exclusive. Other plants which may benefit by application of the compositions and methods of the present invention will be readily determined by those skilled in the art.

The methods and compositions of the present invention may be used to enhance growth in juvenile and mature plants, as well as cuttings, stolons, bulbs, rhizomes, micropropagative tissue, calli, protocorms, and seeds. Generally, however, it is desirable that, for foliar applications, the plants include at least the sprouted cotyledon (i.e., the "seed leaves") and preferably at least two additional expanded true leaves. Sprouted cotyledon and two expanded leaves are also preferred for root applications because the leaf development is, to some extent, indicative of root development. In general, roots may be treated because many plant growth regulators are transported up to shoots from roots.

I. Methods and Formulations

The present invention provides methods and formulations for treating plants, for increasing the amount of ammonium and for enhancing the growth of the plant using polyacylglycosides and/or polyalkylglycosides. These methods generally involve the application of a formulation, comprising polyacylglycosides and/or polyalkylglycosides, preferably with a phytocatalyst comprising a high concentration of ammonium, to the plant.

A. Polyacylglycosides and polyalkylglycosides

For high potency response, the polyacylglycoside and polyalkylglycoside compounds may be applied to plants, in accordance with the methods and compositions of this invention to treat the plants and enhance plant growth and to safen high concentrations of phytocatalysts. Examples of preferred polyacylglycosides and polyalkylglycosides, include, but are not limited to, pentaacetylglucopyranose, tetraacetylglucoside, triacetyladenosine, pentaacetylmannopyranose, pentaacetylgalactopyranose, phenyltetraacetylglucoside, tetramethylglucoside and sucrose octaacetate. Suitable polyacylglycosides and polyalkylglycosides include all isomers, metabolites, salts, hydrates, esters, amines, surfactant-linked derivatives and other suitable biologically or chemically equivalent derivatives and combinations thereof. For example, preferred amine derivatives include polyacylglycosamines, such as glucosamine-(acetate)$_5$. The effective amount of the safening compounds, herein described, at 20 gallons per acre volume of application, is between about 1 and 10,000 ppm and more preferably between about 150 ppm and 1,500 ppm.

For example, tetraacetylglucoside (TAG) is active between about 1 mM to 6 mM concentration. One millimolar concentration is equivalent to about 348 ppm concentration. The preferred amount of tetraacetylglucoside is between about 100 ppm and 3000 ppm concentration and more preferably between about 250 ppm and 750 ppm. TAG typically requires Fe, Mn, ammonium ions and wetting agents to support activation and leaf penetration. As another example, pentaacetylglycoside has an effective range between about 3 ppm to 3000 ppm, and a preferred range between about 100 ppm and 1500 ppm at 20 gallons per acre application volume. As an example of a polyacylglycosamine, glucosamine-(acetate)$_5$ likewise has an effective range between about 3 ppm to 3000 ppm and a preferred range between about 100 and 1500 ppm.

B. Phytocatalyst

High concentrations of phytocatalysts, which preferably comprise soluble ammoniacal nitrogen, manganese and iron, are safened for treating plants and enhancing plant growth, using the methods and formulations of the invention, by mixing and applying the phytocatalysts with one or more compounds selected from the safening compounds described above, including, polyacylglycosides and polyalkylglycosides.

The methods and formulations of the invention effectively safen high concentrations of ammonium, in a range between about 500 ppm to 2500 ppm of ammonium ions, for treating plants and enhancing plant growth, by mixing one or more the above described safening compounds with ammonium ions, preferably in a mixture comprising ammonium ions at a concentration between about 800 to 1800 ppm, and applying a suitable volume of the resulting mixture to one or more plants. Specific examples of ammoniacal nitrogen compounds include, but are not limited to, ammonium salts such as ammonium formate, ammonium citrate, ammonium lactate, ammonium salicylate, ammonium nitrate, ammonium sulfate and the like; urea-compounds such as urea, urea-formaldehyde; Triazone® and other Schiff-base compounds; quaternary amines; amino acids such as glycine, glutamine, tyrosine; protein; peptide; manure; fish meal; other sewage-based fertilizers; night soil; guano; nucleotide; purine; pyrimidine; amide; and imide; as well as, metabolites, and all salts, hydrates, esters, amines, surfactant-linked derivatives, and other biologically or chemically equivalent derivatives thereof and combinations thereof.

The preferred methods and formulations of the invention for rendering high concentrations of manganese safe for plant growth, are achieved by mixing one or more of the safening compounds with manganese, preferably in a mixture comprising manganese at a concentration between about 2 to 100 ppm, and applying a suitable volume of the resulting mixture to one or more plants. The concentration of manganese is preferably between about 2 to 100 ppm generally, and specifically, 2 to 15 ppm for root application and 15 to 75 ppm for shoot application. Specific examples of soluble manganese include manganese chelates such as Mn-EDTA, Mn-HEDTA, Mn-ascorbate, and the like; and manganese salts such as manganese chloride, and the like; listed hereinabove as well as, metabolites, and all salts, hydrates, esters, amines, surfactant-linked derivatives, and other biologically or chemically equivalent derivatives thereof and combinations thereof.

Specific examples of soluble iron include iron chelate such as Fe-EDTA, Fe-HEDTA, Fe-citrate, and the like; and ferric salts such as ferric chloride, ferric ammonium sulfate and the like; and ferrous salts such as ferrous sulfate and the like; listed hereinabove as well as, metabolites, and all salts, hydrates, esters, amines, surfactant-linked derivatives, and other biologically or chemically equivalent derivatives thereof and combinations thereof.

The following is an example of the preferred phytocatalyst formulation for use with the methods and formulations of the invention.

PHYTOCATALYST EXAMPLE

Foliar

| Component | Preferred concentration |
| --- | --- |
| (NH$_4$) | 100 mM ∓ 20% |
| Mn | 30 ppm ∓ 20% |
| Fe | 15 ppm ∓ 50% |

The above phytocatalyst formulation is calibrated to 20 gallons per acre for a standard foliar application rate per volume.

Generally, the formulations of the invention are mixed by dissolving the phytocatalysts and safening compounds in tepid (50° C. to 80° C.) water by mixing for 15 minutes or longer. Solubility of the formulations will increase at lower temperatures, (e.g. 25° C.) by adding compatible organic solvents such as acetic acid, acetal, alkyl acetate, benzene, carbon tetrachloride, toluene, paraldehyde, ketone or alcohol.

For foliar applications, especially those applications using glucose pentaacetate, the preferred surfactant is Hamposyl® AC, which is an ammonium salt of cocoyl sarcosinate, available from Hampshire Chemical Company. This ammonium salt provides a source for both the ammonium ion and fatty acid chains to effectively increase the overall potency of the glucose pentaacetate. Other suitable ammonium salts, such as ammonium lauryl sulfate, may be used. These surfactants are active in the methods and formulations of the invention in a range of 1 g/l to 2 g/l, and preferably in an amount about 1.5 g/l when calibrated at 20 gallons per acre standard volume of foliar exposure.

C. PGR

Plant growth regulators (PGRs) are compounds which generally occur naturally in plants. However, PGRs have also been applied exogenously treat crops and to enhance yields, yet producing only mixed results. According to the methods, compositions, and systems of the present invention, crop yields may be enhanced effectively and consistently by providing the safening compounds and phytocatalyst with an additional PGR component, such as an auxin.

Any number of suitable PGRs such as cytokinins, gibberellins and brassinolides, which will be readily determinable by those skilled in the art may be utilized as a PGR component of the methods, formulations, and systems of the present invention.

D. Application

When applied at relatively high concentrations, the phytocatalysts and safening compounds, with or without one or more of the other components described above, are useful in the methods of the invention for treating plants and enhancing plant growth.

Typically, the safening compound is co-applied with the phytocatalyst component to achieve beneficial results in the methods for treating plants, enhancing yield, and increasing signaling to growth in photosynthetic plants. The phytocatalyst and the safening compound may be applied separately, or formulated together and then applied, to the roots and/or the shoots in any combination or sequence such as those described above. The reverse orders may be applicable, but are not preferred. When the phytocatalyst and safening compounds are separately applied, they are preferably applied at or near the same time, and generally one is applied within a four hour period of the other, preferably within an hour period, more preferably within a half hour period and most preferably within a quarter hour period. In the preferred method, the phytocatalyst plus the safening compounds are formulated into a single composition and thereby simultaneously applied to the plant.

Although the components may be applied in a solid form, it is often advantageous to provide the formulation in liquid form, such as by solubilizing the components in an aqueous or agronomically suitable organic solvent or carrier to produce aqueous or organic solutions for application to the plant. The amount of safening compounds and phytocatalyst, which is solubilized in the carrier, will depend upon the particular compounds selected and the method of application. For example, the safening compounds may be solubilized in the carrier by adding the safening compounds to the carrier, such as acetone or ethyl acetate, and allowing them to dissolve. In some instances, the application of stirring, agitation and heat (50° C. to 80° C.) may facilitate the dissolution of the safening compounds in water.

A polyacylglycoside, such as pentaacetylmannoside, may be formulated with the phytocatalyst formulation, such as ammoniacal nitrogen, soluble Mn and soluble Fe. Typically, the polyacylglycoside is applied as an aqueous solution having a concentration in the range of between about 25 ppm and about 2,500 ppm by weight of the composition inclusive, depending on the particular polyacylglycoside utilized.

In the embodiment wherein the safening compounds and the phytocatalyst are combined into a single composition, the composition includes an aqueous or agronomically suitable organic solution having solubilized, dispersed, or otherwise contained therein, an amount of the safening compounds that induces cellulose synthesis in the plant and an aqueous solution having solubilized, dispersed or otherwise contained therein, an amount of the phytocatalyst that induces enzyme enhancement in the plant. The solution containing the safening compounds and the phytocatalyst may be prepared using the general techniques set forth above for solubilizing the safening compounds or phytocatalyst alone. Compositions containing both the safening compounds and the phytocatalyst are advantageous in that they permit the one-step application of both components to the plant.

While the compositions of the present invention may consist essentially of the aqueous solutions of the safening compounds and phytocatalyst, with or without one or more additives; oil soluble compounds may be formulated in agronomically suitable organic solvents. For example, pentaacetylgalactopyranose and the phytocatalyst may be formulated as ethylacetate concentrates with paraffin oil as the spreader for application in appropriate crop emulsions, hydrosols or organic films.

The compositions of the present invention may also include any of a wide variety of agronomically suitable additives, adjuvants, or other ingredients and components which improve or at least do not hinder the beneficial effects of the compositions of the present invention (hereinafter "additives"). Generally accepted additives for agricultural application are periodically listed by the United States Environmental Protection Agency. For example, foliar compositions may contain a surfactant and a spreader present in an amount sufficient to promote wetting, emulsification, even distribution and penetration of the active substances. Spreaders are typically organic alkanes, alkenes or polydimethylsiloxanes which provide a sheeting action of the treatment across the phylloplane. Suitable spreaders include paraffin oils, trimethylsilylglucoside and polyalkyleneoxide polydimethylsiloxanes. Suitable surfactants include anionic, cationic, nonionic, and zwitterionic detergents, ammonium lauryl sulfate, amine ethoxylates, alkyl phenol ethoxylates, phosphate esters, PEG, polymerics, polyoxyethylene fatty acid esters, polyoxyethylene fatty diglycerides, sorbitan fatty acid esters, alcohol ethoxylates, sorbitan fatty acid ester ethoxylates, ethoxylated alkylamines, quaternary amines, sorbitan ethoxylate esters, alkyl polysaccharides, block copolymers, EOPO copolymers, trisiloxanes, CHELACTANTS™ and blends. Surfactant preference is for polyalkylene oxides, polyalkylene glycols, and alkoxylate-fatty acids. Blends are highly effective such as the sarcosinate/block copolymer surfactant Hamposyl® AC+Pluronic® blend, which use is demonstrated in the examples. Preferred commercial aqueous surfactants include Hampshire LED3A; HAMPOSYL®; TEEPOL®; TWEEN®; TRITON®; LATRON™; PLURONIC®; TETRONIC®; SURFONIC®; SYNPERONIC®; ADMOX®; DAWN®, and the like. Commercial emulsifiers for combination with organic solvent formulations include WITCANOL®, RHODASURF®, TERGITOL® and TWEEN®. Commercial spreaders include paraffin oil, TEGOPREN®, AGRIMAX™, DOW CORNING® 211, X-77®, SILWET® and the like. Penetrants such as sodium dodecylsulfate, formamides and lower aliphatic alcohols, may be used. Alkoxylation of an active component or otherwise chemically modifying the active components by incorporating a penetrant substance is useful because formulation without additional surfactant is achieved.

Large polyalkyl polysaccharide molecules, such as sucrose octaacetate or tetradecylmaltoside, pose problems related to cellular penetration. Addition of diatomaceous earth, carborundum, fine bentonite, clay, fine sand or alumina may be added to the compositions of the present invention to scratch the leaf surface and assist with penetration. Small quantities (0.03–0.3%) of sterile diatomaceous earth are preferred additions to the adjuvant formulation to enhance penetration. In some cases, such as cabbage, in which cells are tough, gentle movement of the diatoms across the leaf surface by mechanical rubbing or high pressure treatments may be employed.

In addition to the foregoing additives, the compositions of the present invention may also advantageously include one or more fertilizers. Suitable fertilizers for inclusion in the compositions, methods and systems of the present invention will be readily determinable by those skilled in the art and include conventional fertilizers containing elements such as nitrogen, phosphorus, potassium, carbon, oxygen and the like. Nitrogenous fertilizers (i.e., fertilizers containing nitrogen) are currently preferred; particularly nitrogenous fertilizers containing ammoniacal nitrogen. Nitrate fertilizers may be included in the methods of the present invention. In particular, in cases requiring foliar fertilizers, ammonium nitrate fertilizers may be utilized. Fertilizers may be fed to plants at any time during or after treatment, through the root and/or the shoot. The amount of fertilizer added to the compositions of the present invention will depend upon the plants to be treated, and the nutrient content of the soil. Typically, the conventional fertilizer is included in an amount between about 0.1% and 2%, preferably between about 0.2% and 1%, and more preferably between about 0.4% and 0.8% by weight of the composition.

In addition to the conventional fertilizers, the compositions of the present invention may also include the novel $C_1$–$C_7$ alkyl glucosides which are the subject of U.S. Pat. No. 5,958,104 and/or the novel cyclic alkyl glycosides which are the subject of U.S. patent application, Ser. No. 09/474,502, filed on Dec. 29, 1999, which is incorporated herein by reference in its entirety.

In addition to formulations comprising one or more iron or nitrogen sources, or high concentrations of manganese, as described in U.S. patent application Ser. No. 09/448,345, filed on Nov. 23, 1999 and incorporated herein by reference, the formulations of the present invention may include any of various secondary nutrients, such as sources of sulfur, calcium, and magnesium; as well as micronutrients, such as boron, cobalt, copper, molybdenum, zinc, nickel, and the like, which are conventionally formulated in foliar fertilizers. Other conventional fertilizer constituents which may be added to the compositions of the present invention include pesticides, herbicides, fungicides, antibiotics, gene therapies and the like.

As noted, the compositions of the present invention may be applied to the plants using conventional application techniques. Plants nearing or at maturity may be treated at any time before and during seed development. Fruit bearing plants may be treated before and after the onset of bud or fruit formation.

The compositions of the present invention may be applied to the plant at a location including leaves, fruit, flowers, shoots, root, seed, and stem. The compositions may be applied to the leaves, seed or stem by spraying the leaves or coating the seeds with the composition. The composition may be applied to the shoot or root by spraying the shoot or root, or dusting the shoot or root, or side-dressing the root with slow-release encapsulations or formulations, or dipping the shoot or root in a bath of the composition, or drenching the soil in which the plant is being cultivated with the composition, or spray-drenching the leaves and stem of the plant such that the soil in which the plant is being cultivated becomes saturated with the composition.

Foliar application (i.e., application of the composition to one or more leaves of the plant) of the compositions of the present invention is currently preferred. The composition will normally be applied to the leaves of the plant using a spray. However, other means of foliar application, such as dipping, dusting, brushing, wicking, misting, electrostatic dispersion and the like of liquids, foams, gels, powders and other formulations may also be employed. Side dressing is also applicable. Foliar sprays can be applied to the leaves of the plant using commercially available spray systems, such as those intended for the application of foliar fertilizers, pesticides, and the like, and available from commercial vendors such as FMC Corporation, John Deere, Valmont and Spraying Systems (TEEJET®). If desired, the safening compounds and phytocatalyst compounds may be applied to plants in rapid sequence from separate nozzles in separate reservoirs. Chemically compatible combined mixtures may be preferred for many applications to produce improved plant growth. High foliar content of safeners and phytocatalyst maintains high rates of growth during day and night, with the greatest response when plants are exposed to water, nutrients, warmth and high light intensity consistent with good agricultural practices. In the embodiment wherein the root and/or shoot is dipped in a bath of the formulation, it is preferred to pulse the application of the formulation of the present invention by dipping the shoot and/or root in the bath containing the formulation for a period of time and then removing the shoot and/or root from the formulation. The dipping period may be from 10 minute to 60 minutes, and is preferably from 15 to 30 minutes.

The formulations of the present invention may also be applied to plant tissues, such as cell suspensions, callus tissue cultures, and micropropagation cultures. Such plant tissues may be treated with the formulations of the present invention by adding the formulation to the culture medium in which the plant tissues are being cultivated. The formulations of the invention may be applied at very low concentrations without surfactant or spreader for treatments of roots and tissue culture.

In the methods of the present invention, the formulations are typically applied in the amount of between about 3 gallons per acre and about 100 gallons per acre, depending upon the application method. For horticulture applications, the formulations are preferably applied in the amount of between about 75 gallons per acre and about 100 gallons per acre. For ground-rig row crop applications, the formulations are preferably applied in the amount of between about 10 gallons per acre and about 40 gallons per acre. As a standard for consistent comparisons, treatments of this invention are calibrated to conventional foliar spray ground rig volumes of 20 gallons per acre. For aerial applications by helicopter or airplane crop dusters, the formulations are preferably applied in the amount of between about 1 gallon per acre and about 5 gallons per acre. The formulations may be applied in a single application, or in multiple applications interrupted by periods of photosynthetic activity. Ornamentals and other tender nursery plants meant for indoor horticulture will frequently require lower concentrations and perhaps more frequent application than outdoor agricultural crops.

In general agricultural practice, withholding pesticidal application to the target crop for 2 days prior to and following treatment is recommended to prevent interference. Suitable light and temperature conditions may be achieved by treating plants at any time of day or night. Hot temperatures, usually above 15° C. and preferably above 30° C., may be required after treatment. The plants should remain exposed to the sunlight or high intensity illumination for a period of time sufficient to allow for incorporation of treatments. Usually, the plants should remain exposed to sunlight or other illumination during daylight photoperiods for at least six hours after treatments. Sufficient nutrients should be present to support healthy growth.

Throughout the growing season after treatments, either sun or artificial illumination should have an intensity and duration sufficient for prolonged high rates of photosynthesis. A minimum suitable illumination intensity is between 200–500 $\mu$mol photosynthetically active quanta (400–700 nm) $m^{-2}s^{-1}$, with direct sunlight normally providing much higher illumination. Prior to treatment, leaf temperature should be sufficiently high for optimal growth, usually between or above 10° C. to 35° C. After treatment, the leaf temperature will normally drop as a consequence of improved transpiration. It is preferable that the plant be exposed to at least a week of intense illumination preferably between 500–800 μmol photosynthetically active quanta $m^{-2}s^{-1}$ following application of the formulations of the present invention.

Formulations according to the present invention may be tailored for specific uses, including enhanced yield; early yield; rapid cycling through growing seasons; aftermarket; rooting; branching; flower retention; fruit optimization.

The following examples are provided to further illustrate the present invention, and should not be construed as limiting thereof. In these examples, Hamposyl® AC, KOH, HCl, ammonia, ammonium hydroxide, manganese EDTA as Versene®, ferric HEDTA as Versenol®, ferric EDTA, Dow Corning® surfactants, and purified water were obtained from Dow Chemical Company. Ethanol (Ethan), ammonium sulfate (($NH_4)_2SO_4$), ammonium nitrate (AMN), methanol (MeOH) and potassium phosphate were obtained from Fisher Scientific. The α-D-glucose pentaacetate, β-D-glucose pentaacetate, tetraacetyl glucoside (TAG) and tetramethyl glucopyranose were obtained from Sigma, as were PGRs. Pluronic® surfactants were obtained from BASF. The α-/β-D-glucose pentaacetate (high β) blend was obtained from Pfanstiehl. In these examples, "l" means liter; "mg" means milligrams; and "g" means grams.

Following are examples of specific compositions according to the present invention, which may advantageously be employed in the methods of the present invention to treat plants and to enhance growth and amounts of signaling agents in plants. The following exemplary compositions are intended to provide further guidance to those skilled in the art, and do not represent an exhaustive listing of compositions within the scope of the present invention.

First Exemplary Polyacylglycoside Formulation

| Composition | Preferred concentration | Broad Range Concentration |
|---|---|---|
| TAG | 3 mM | 1 to 6 mM |

The above listed polyacylglycoside was calibrated to a foliar application volume of 20 gallons per acre and included sources of Fe, Mn, $NH_4$ and wetting agents to support activation and leaf penetration. Specifically, the TAG was formulated with 50 mM ammonium sulfate, 20 ppm manganese and 20 ppm iron. The solution was applied to radish foliage with 1.2 g/l surfactant. The application elicited a statistically significant increase in radish yield. TAG, at 3 mM concentration, is approximately 100 times more potent than a simple straight chain monoalkyl glucoside such as methyl glycoside.

Second Exemplary Polyacylglycoside Formulation

| Composition | Concentration |
|---|---|
| TAG | 0.35 g/l |
| $NH_4NO_3$ | 8 g/l |
| MnEDTA | 0.2 g/l |
| FeEDTA | 0.2 g/l |
| Hamposyl® AC | 1.2 g/l |

The above formulation was calibrated to a foliar application to crops at 20 gallons per acre and elicited a statistically significant increase in yield.

Third Exemplary Polyacylglycoside Formulation

| Composition | Preferred concentration | Broad Range Concentration |
|---|---|---|
| α/β-D-glucose pentaacetate | 0.5 g/l | 0.1 g/l to 5 g/l |

The above listed polyacylglycoside blend, obtained from Pfanstiehl, was calibrated to a foliar application volume of 20 gallons per acre and included sources of Fe, Mn, $NH_4$ and wetting agents to support activation and leaf penetration. The application elicited a statistically significant increase in yield of about 10%, which was visibly discernible within 16–24 hours after application.

Fourth Exemplary Polyacylglycoside Formulation

| Composition | Concentration |
|---|---|
| α-D-glucopyranose pentaacetate | 0.5 g/l |
| Pluronic® L-92 surfactant | 0.8 g/l |
| Dow Corning® 211 | 0.4 g/l |

Dissolve the formulation in 1 liter of hot water (60° C.) with stirring. The above formulation was calibrated to a foliar application to crops at 20 gallons per acre and compared to control plants which were sprayed with the same formulation minus α-D-glucopyranose pentaacetate. The application elicited a statistically significant increase in yield.

Fifth Exemplary Polyacylglycoside Formulation

| Composition | Concentration |
|---|---|
| β-D-glucose pentaacetate | 260 mg/l |
| $(NH_4)_2SO_4$ | 6.7 g/l |
| MnEDTA | 0.2 g/l |
| FeEDTA | 0.2 g/l |
| Hamposyl® AC, ammonium salt | 0.7 g/l |
| Pluronic® L-92 | 0.7 g/l |

The above formulation was dissolved in 1 liter of water and applied to corn at a three to eight leaf state at 20 gallons per acre. The application elicited a statistically significant increase in yield.

First Exemplary Polacylglycosamine Formulation

| Composition | Concentration |
|---|---|
| β-D-glucosamine pentaacetate | 500 ppm |
| $(NH_4)_2SO_4$ (Fisher/Acros) | 1800 ppm |
| Versene® (MnEDTA) | 30 ppm Mn |
| Versenol® (FeHEDTA) | 15 ppm Fe |
| Hamposyl® AC | 1.5 gm/liter |

The above formulation was mixed in 1 liter of tepid (50° C.) water and stirred until dissolved. The mixture was then applied to Canoe at a two leaf stage as a foliar spray calibrated to a volume of 20 gallons per acre or 1.8 g of diluted solutes per 1000 square centimeters. The application elicited a statistically significant increase in yield.

| First Exemplary Polyalkylglycoside Formulation | |
| --- | --- |
| Composition | Concentration |
| Tetramethyl-D-glucopyranose | 71 ppm |
| $(NH_4)_2SO_4$ | 1800 ppm |
| MnEDTA | 28 ppm |
| FeHEDTA | 18 ppm |
| Hamposyl ® AC/block copolymer surfactant blend | 1800 ppm |

The above formulation was dissolved in water and calibrated to a volume of 20 gallons per acre foliar spray and applied to corn. The application elicited a statistically significant increase in yield.

In instances where nutrients are not optimized for a given crop, supplement each liter of the exemplary formulations with the following minimal plant nutrients:

| | |
| --- | --- |
| Ammonium sulfate | 7 g |
| Potassium phosphates | 1 g (adjust to pH 7 to pH 8) |
| MnEDTA (12% Mn) | 0.2 g |
| FeEDTA (13% Fe) | 0.2 g |

Although specific features of the invention are described with respect to one example and not others, this is for convenience only as some feature of one described example may be combined with one or more of the other examples in accordance with the methods and formulations of the invention.

Other permutations of the methods and formulations of the invention will occur to those skilled in the art and are within the following claims:

What is claimed is:

1. A method for treating plants and enhancing plant growth, comprising the steps of,
applying one or more phytocatalysts comprising ammonium ions at a concentration between about 500 parts per million (ppm) and 2500 ppm to said plants; and
applying an effective amount of one or more compounds selected from a group consisting of polyacylglycosides and polyalkylglycosides; isomers, metabolites, salts, hydrates, esters, amines, and derivatives of said polyacylglycosides and said polyalkylglycosides; and combinations thereof; to said plants.

2. The method of claim 1, wherein one or more of said compounds comprises polyacylglycoside.

3. The method of claim 2, wherein one or more of said compounds comprises pentaacetylglycoside.

4. The method of claim 3, wherein an effective amount of said pentaacetylglycoside is between about 3 ppm to 3000 ppm.

5. The method of claim 4, wherein an effective amount of said pentaacetylglycoside is between about 100 ppm and 1500 ppm.

6. The method of claim 2, wherein an effective amount comprises polyacylglycosides between about 100 ppm to 10,000 ppm concentration.

7. The method of claim 1, wherein said effective amount comprises between about 100 ppm to 10,000 ppm concentration.

8. The method of claim 1, wherein one or more of said phytocatalysts further comprises one or more nutrients selected from a group consisting of iron and manganese.

9. The method of claim 8, wherein said manganese is applied at a concentration between about 2 to 100 ppm.

10. The method of claim 1, further comprising the step of applying one or more plant growth regulators to said plant.

11. The method of claim 1, further comprising applying said compounds to said plants as a foliar formulation with one or more surfactants.

12. The method of claim 11, wherein one or more of said surfactants comprises an ammonium salt.

13. The method of claim 12, wherein one or more of said surfactants comprises an ammonium salt of one or more fatty acid sarcosinates.

14. The method of claim 12, wherein said ammonium salt of said surfactant is applied in an amount between about 1 to 2 grams/liter.

15. A method for treating plants and for enhancing plant growth, comprising the steps of,
applying one or more phytocatalysts comprising ammonium ions at a concentration between about 500 parts per million (ppm) and 2500 ppm to said plants; and
applying an effective amount of one or more compounds selected from a group consisting of, $(acyl)_n$glycosides, wherein n=2 to 5; isomers, metabolites, salts, hydrates, esters, amines, and derivatives of said (acyl)$_n$glycosides; and combinations thereof, to said plants.

16. The method of claim 15, wherein one or more of said compounds comprises β-D-glucose-(acetate)$_5$.

17. The method of claim 15, wherein one or more of said compounds comprises α-D-glucose-(acetate)$_5$.

18. A method for treating plants and for enhancing plant growth, comprising the steps of,
applying one or more phytocatalysts comprising ammonium ions at a concentration between about 500 parts per million (ppm) and 2500 ppm to said plants; and
applying an effective amount of one or more compounds selected from a group consisting of, (acyl)$_n$glycosamines, wherein n=2 to 5; isomers, metabolites, salts, hydrates, esters, amines, and derivatives of said (acyl)$_n$glycosamines; and combinations thereof, to said plants.

19. The method of claim 18, wherein one or more of said compounds comprises β-D-glucosamine pentaacetate.

20. The method of claim 18, wherein one or more of said phytocatalysts further comprises one or more nutrients selected from a group consisting of iron and manganese.

21. The method of claim 20, wherein said manganese is applied at a concentration between about 2 to 100 ppm.

22. The method of claim 19, further comprising the step of applying one or more surfactants.

23. The method of claim 22, wherein one or more of said surfactants comprises ammonium salt.

24. A method for treating plants and for enhancing plant growth, comprising the steps of,
applying one or more phytocatalysts comprising ammonium ions at a concentration between about 500 parts per million (ppm) and 2500 ppm to said plants; and
applying an effective amount of one or more compounds selected from a group consisting of, (methyl)$_n$glycosides, wherein n=2 to 5; and isomers, metabolites, salts, hydrates, esters, amines and derivatives of said (methyl)$_n$glycosides; to said plants.

25. The method of claim 24, wherein one or more of said compounds comprises (methyl)$_4$-D-glucopyranose.

26. The method of claim 24, wherein one or more of said phytocatalysts further comprises one or more nutrients selected from a group consisting of iron and manganese.

27. A formulation for treating plants and enhancing plant growth, comprising, one or more phytocatalysts comprising ammonium ions at a concentration between about 500 parts per million (ppm) and 2500 ppm; and an effective amount of one or more compounds selected from a group consisting of polyacylglycosides and polyalkylglycosides; isomers, metabolites, salts, hydrates, esters, amines, and derivatives of said polyacylglycosides and said polyalkylglycosides; and combinations thereof.

28. The formulation of claim 27, wherein one or more of said compounds comprises polyacylglycoside.

29. The formulation of claim 28, wherein one or more of said compounds comprises pentaacetylglycoside.

30. The formulation of claim 29, wherein an effective amount of said pentaacetylglycoside is between about 3 ppm to 3000 ppm.

31. The formulation of claim 30, wherein an effective amount of said pentaacetylglycoside is between about 100 ppm and 1500 ppm.

32. The formulation of claim 28, wherein an effective amount comprises polyacylglycosides between about 100 ppm to 10,000 ppm concentration.

33. The formulation of claim 27, wherein said effective amount comprises between about 100 ppm to 10,000 ppm concentration.

34. The formulation of claim 27, wherein one or more of said phytocatalysts further comprises one or more nutrients selected from a group consisting of iron and manganese.

35. The formulation of claim 34, wherein said manganese is applied at a concentration between about 2 to 100 ppm.

36. The formulation of claim 27, further comprising one or more plant growth regulators.

37. The formulation of claim 27, further comprising one or more surfactants.

38. The formulation of claim 37, wherein one or more of said surfactants comprises an ammonium salt.

39. The formulation of claim 38, wherein one or more of said surfactants comprises an ammonium salt of one or more fatty acid sarcosinates.

40. The formulation of claim 38, wherein said ammonium salt of said surfactant is an amount between about 1 to 2 grams/liter.

41. The formulation of claim 38, wherein said ammonium salt of said surfactant comprises ammonium lauryl sulfate.

42. A formulation for treating plants and for enhancing plant growth, comprising, one or more phytocatalysts comprising ammonium ions at a concentration between about 500 parts per million (ppm) and 2500 ppm; and an effective amount of one or more compounds selected from a group consisting of, (acyl)$_n$glycosides, wherein n=2 to 5; isomers, metabolites, salts, hydrates, esters, amines, and derivatives of said (acyl)$_n$glycosides; and combinations thereof.

43. The formulation of claim 42, wherein one or more of said compounds comprises β-D-glucose-(acetate)$_5$.

44. The formulation of claim 42, wherein one or more of said compounds comprises α-D-glucose-(acetate)$_5$.

45. A formulation for treating plants and for enhancing plant growth, comprising, one or more phytocatalysts comprising ammonium ions at a concentration between about 500 parts per million (ppm) and 2500 ppm; and an effective amount of one or more compounds selected from a group consisting of, (acyl)$_n$glycosamines, wherein n=2 to 5; isomers, metabolites, salts, hydrates, esters, amines, and derivatives of said (acyl)$_n$glycosamines; and combinations thereof.

46. The formulation of claim 45, wherein one or more of said compounds comprises β-D-glucosamine pentaacetate.

47. The formulation of claim 45, wherein one or more of said phytocatalysts further comprises one or more nutrients selected from a group consisting of iron and manganese.

48. The formulation of claim 47, wherein said manganese is at a concentration between about 2 to 100 ppm.

49. The formulation of claim 45, further comprising one or more surfactants.

50. The formulation of claim 49, wherein one or more of said surfactants comprises ammonium salt.

51. A formulation for treating plants and for enhancing plant growth, comprising, one or more phytocatalysts comprising ammonium ions at a concentration between about 500 parts per million (ppm) and 2500 ppm; and an effective amount of one or more compounds selected from a group consisting of, (methyl)$_n$glycosides, wherein n=2 to 5; and isomers, metabolites, salts, hydrates, esters, amines and derivatives of said (methyl)$_n$glycosides.

52. The formulation of claim 51, wherein one or more of said compounds comprises (methyl)$_4$-D-glucopyranose.

53. The formulation of claim 51, wherein one or more of said phytocatalysts further comprises one or more nutrients selected from a group consisting of iron and manganese.

54. A method for treating plants and enhancing plant growth, comprising the step of, applying an effective amount of one or more polyacylglycosides to said plants.

55. A method for treating plants and enhancing plant growth, comprising the step of, applying an effective amount of glucose pentaacetate to said plants.

56. The method of claim 55, wherein said glucose pentaacetate comprises β-D-glucose-(acetate)$_5$.

57. The method of claim 56, wherein said glucose pentaacetate further comprises α-D-glucose-(acetate)$_5$.

58. The method of claim 56, wherein said effective amount of said glucose pentaacetate is capable of eliciting about a 10% increase in yield within 24 hours after said amount is applied.

59. A formulation for treating plants and for enhancing plant growth, comprising, an effective amount of one or more compounds selected from a group consisting of, (acyl)$_n$glycosides, wherein n=2 to 5; isomers, metabolites, salts, hydrates, esters, amines, and derivatives of said (acyl)$_n$glycosides; and combinations thereof.

60. The formulation of claim 59, wherein one or more of said compounds comprises β-D-glucose-(acetate)$_5$.

61. The formulation of claim 59, wherein one or more of said compounds comprises α-D-glucose-(acetate)$_5$.

62. The formulation of claim 59, wherein one or more of said compounds comprises α,β-D-glucose-(acetate)$_5$.

63. The formulation of claim 59, wherein said effective amount of said compound is capable of eliciting about a 10% increase in yield within 24 hours after said amount is applied.

* * * * *